(12) United States Patent
Bahmer

(10) Patent No.: US 9,999,771 B2
(45) Date of Patent: Jun. 19, 2018

(54) PREFITTING EVALUATION OF COCHLEAR IMPLANT PATIENTS

(71) Applicant: MED-EL Elektromedizinische Geraete GmbH, Innsbruck (AT)

(72) Inventor: Andreas Bahmer, Aschaffenburg (DE)

(73) Assignee: MED-EL Elektromedizinische Geraete GmbH, Innsbruck (AT)

(*) Notice: Subject to any disclaimer, the term of this patent is extended or adjusted under 35 U.S.C. 154(b) by 454 days.

(21) Appl. No.: 14/750,087

(22) Filed: Jun. 25, 2015

(65) Prior Publication Data

US 2015/0374986 A1 Dec. 31, 2015

Related U.S. Application Data

(60) Provisional application No. 62/016,793, filed on Jun. 25, 2014, provisional application No. 62/054,503, filed on Sep. 24, 2014.

(51) Int. Cl.
*A61N 1/32* (2006.01)
*A61N 1/36* (2006.01)
(Continued)

(52) U.S. Cl.
CPC ..... *A61N 1/36032* (2013.01); *A61N 1/36036* (2017.08); *A61N 1/37241* (2013.01); *H04R 25/70* (2013.01); *H04R 2225/67* (2013.01)

(58) Field of Classification Search
CPC ............ A61N 1/36032; A61N 1/36036; A61N 1/37241; H04R 25/70; H04R 2225/67
(Continued)

(56) References Cited

U.S. PATENT DOCUMENTS 6,289,247 B1 * 9/2001 Faltys ................ A61N 1/36036
607/55
2010/0145411 A1 6/2010 Spitzer
(Continued)

FOREIGN PATENT DOCUMENTS

WO    WO 2013/142844    9/2013

OTHER PUBLICATIONS

Gaudrain, Etienne, et al. "Temporal Regularity Detection and Rate Discrimination in Cochlear-Implant Listeners". Dec. 10, 2015. Journal of the Association for Research in Otolaryngology. vol. 18. pp. 387-397.*
(Continued)

*Primary Examiner* — Michael Carey
(74) *Attorney, Agent, or Firm* — Sunstein Kann Murphy & Timbers LLP

(57) ABSTRACT

Arrangements are described for assessing potential fitting processes for a cochlear implant patient. A test stimulation sequence at a given test frequency is delivered to the cochlear implant patient. The test stimulation sequence includes jittered stimulation periods when the test frequency varies due to a jitter variation component, and unjittered stimulation periods when the test frequency is constant without a jitter variation component. At least two different responses of the cochlear implant to the test stimulation sequence are measured in parallel. The different responses include an objective electrophysiological response, and a subjective psychophysical response. A correlation between the different responses is evaluated to determine an appropriate fitting process for the cochlear implant patient.

28 Claims, 7 Drawing Sheets

(51) Int. Cl.
*A61N 1/372* (2006.01)
*H04R 25/00* (2006.01)

(58) Field of Classification Search
USPC .............................................. 607/55, 56, 57
See application file for complete search history.

(56) References Cited

U.S. PATENT DOCUMENTS

| | | | |
|---|---|---|---|
| 2011/0082519 A1* | 4/2011 | Strahl ................ | A61N 1/37247 607/57 |
| 2012/0029594 A1* | 2/2012 | Chapa ................ | A61N 1/37288 607/57 |
| 2013/0079845 A1 | 3/2013 | Nopp et al. | |
| 2015/0264492 A1* | 9/2015 | Laudanski ............... | H04R 1/10 381/60 |

OTHER PUBLICATIONS

Bahmer, et al, "Recording and online analysis of auditory steady state responses (ASSR) in Matlab", *Journal of Neuroscience Methods*, vol. 187, pp. 105-113 (2010).

Hofmann, et al, "Electrically Evoked Auditory Steady State Responses in Cochlear Implant Users", *Journal of the Association of Research in Otolaryngology*, 11:267-282 (2010).

International Searching Authority, Authorized Officer Blaine R. Copenheaver, International Search Report and Written Opinion, PCT/US2015/037638, dated Sep. 23, 2015, 12 pages.

\* cited by examiner

PREFITTING EVALUATION OF COCHLEAR IMPLANT PATIENTS

This application claims priority from U.S. Provisional Patent Application 62/016,793, filed Jun. 25, 2014, and from U.S. Provisional Patent Application 62/054,503, filed Sep. 24, 2014, both of which are incorporated herein by reference.

TECHNICAL FIELD

The present invention relates to evaluation of potential fitting techniques for cochlear implant patients.

BACKGROUND ART

A normal ear transmits sounds as shown in FIG. 1 through the outer ear 101 to the tympanic membrane (eardrum) 102, which moves the bones of the middle ear 103, which in turn vibrate the oval window and round window openings of the cochlea 104. The cochlea 104 is a long narrow duct wound spirally about its axis for approximately two and a half turns. The cochlea 104 includes an upper channel known as the scala vestibuli and a lower channel known as the scala tympani, which are connected by the cochlear duct. The scala tympani forms an upright spiraling cone with a center called the modiolar where the spiral ganglion cells of the acoustic nerve 113 reside. In response to received sounds transmitted by the middle ear 103, the fluid filled cochlea 104 functions as a transducer to generate electric pulses that are transmitted to the cochlear nerve 113, and ultimately to the brain. Hearing is impaired when there are problems in the ability to transduce external sounds into meaningful action potentials along the neural substrate of the cochlea 104.

In some cases, hearing impairment can be addressed by a cochlear implant that electrically stimulates auditory nerve tissue with small currents delivered by multiple electrode contacts distributed along an implant electrode. FIG. 1 shows some components of a typical cochlear implant system where an external microphone provides an audio signal input to an external signal processing stage 111 which implements one of various known signal processing schemes. The processed signal is converted by the external signal processing stage 111 into a digital data format, such as a sequence of data frames, for transmission into a receiver processor in an implant housing 108. Besides extracting the audio information, the receiver processor in the implant housing 108 may perform additional signal processing such as error correction, pulse formation, etc., and produces a stimulation pattern (based on the extracted audio information) that is sent through wires in an electrode lead 109 to an implanted electrode array 110.

The electrode array 110 penetrates into the cochlea 104 through a surgical opening called a cochleostomy. The electrode array 110 has multiple electrode contacts 112 on or recessed slightly below its outer surface for applying one or more electrical stimulation signals to target audio neural tissue within the cochlea 104. The extra-cochlear electrode lead 109 that goes from the implant housing 108 to the cochleostomy opening usually has no electrical contacts except perhaps a ground electrode and it encloses connecting wires that deliver electrical stimulation signals to the electrode contacts on the electrode array 110.

After implantation, a cochlear implant system needs to be adjusted for each specific patient in a clinical fitting process. Information on patient performance while using the implant system is needed to compare different processing algorithms and/or processing parameters with regards to any differences in the performance of the system or the experience of the patient. This information can be obtained subjectively by feedback from the patient and/or by different objective measurement methods.

SUMMARY

Embodiments of the present invention include systems and methods for assessing potential fitting processes for a cochlear implant patient. A test stimulation generator delivers to the cochlear implant patient a test stimulation sequence at a given test frequency. The test stimulation sequence includes jittered stimulation periods in which the test frequency varies due to a jitter variation component, and unjittered stimulation periods in which the test frequency is constant without a jitter variation component. A response measurement module measures in parallel at least two different responses of the cochlear implant to the test stimulation sequence. The response measurement module includes an objective measurement submodule that measures an objective electrophysiological response, and a subjective measurement submodule that measures a subjective psychophysical response. A correlation evaluation module evaluates a correlation between the different responses to determine an appropriate fitting process for the cochlear implant patient.

In further specific embodiments, the correlation evaluation module may include a fitting process selection submodule that determines an objective electrophysical fitting process as the appropriate fitting process when the correlation is evaluated to be sufficient. The fitting process selection submodule may further determine a subjective psychophysical fitting process as the appropriate fitting process when the correlation is evaluated to be insufficient.

The subjective measurement submodule may specifically measure the subjective psychophysical response based on perception by the cochlear implant patient of the jitter variation component. The objective electrophysical response measured by the objective response submodule may include an auditory steady-state response (ASSR) such as an acoustically evoked ASSR (AASSR) and/or an electrically evoked ASSR (EASSR). And the test stimulation generator may specifically deliver an acoustic and/or electric test stimulation sequence to the cochlear implant patient.

The test stimulation generator may generate a constant amount of variation in the test frequency in all of the jittered stimulation periods, or it may change the amount of variation in the test frequency between different jittered stimulation periods. The test stimulation generator may deliver stimulation periods with uniform time durations, or stimulation periods with different time durations, and/or the test stimulation generator may deliver the jittered stimulation periods and the unjittered stimulation periods with equal time durations.

DETAILED DESCRIPTION

Embodiments of the present invention are directed to a pre-fitting evaluation of whether a patient who has received a cochlear implant can be fitted based on an objective electrophysical measurement such as auditory steady-state response (ASSR) measurements, or whether to instead perform the fitting based on state-of-the-art psychophysical or other objective fitting methods. An electrophysical fitting such as one based on ASSR may be used exclusively or in addition to other standard fitting methods. The pre-fitting test adds a jitter variation component to the test stimulus and then evaluates the correlation between an objective ASSR of a patient and their simultaneous subjective responses to psychophysical measurements.

In the following unless explicitly specified differently, the auditory steady state response ASSR can be either or both electrically evoked ASSR (EASSR) and acoustically evoked ASSR (AASSR). Jitter variation in EASSR means a sequence of stimulus pulses with varied distance (time) between the individual pulses. Jitter variation in AASSR means variation of the test modulation frequencies as explained above.

Figure 1:
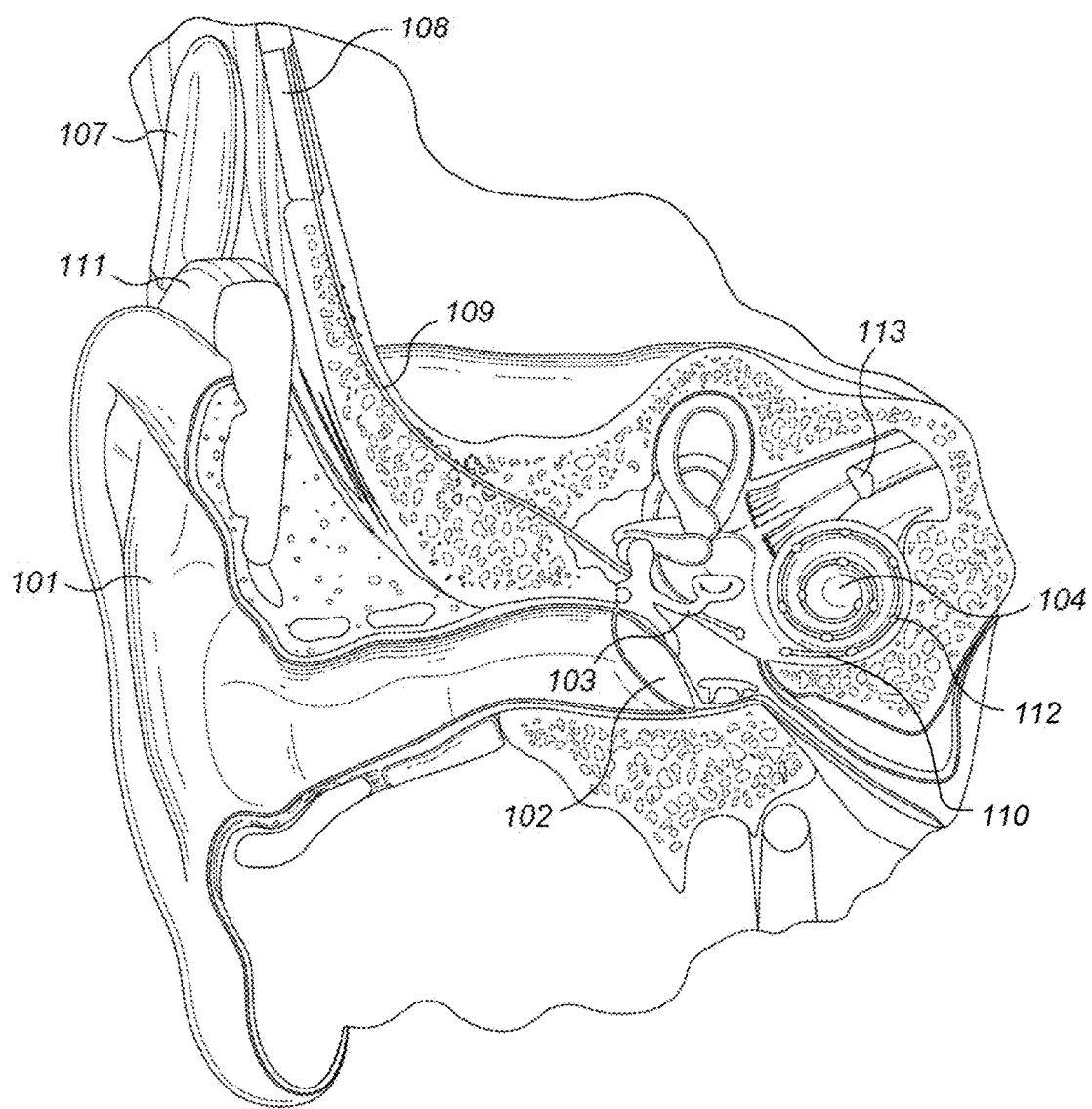
FIG. 1 shows various anatomical structures of the human ear and components of a typical cochlear implant system in relation thereto.
Figure 2:
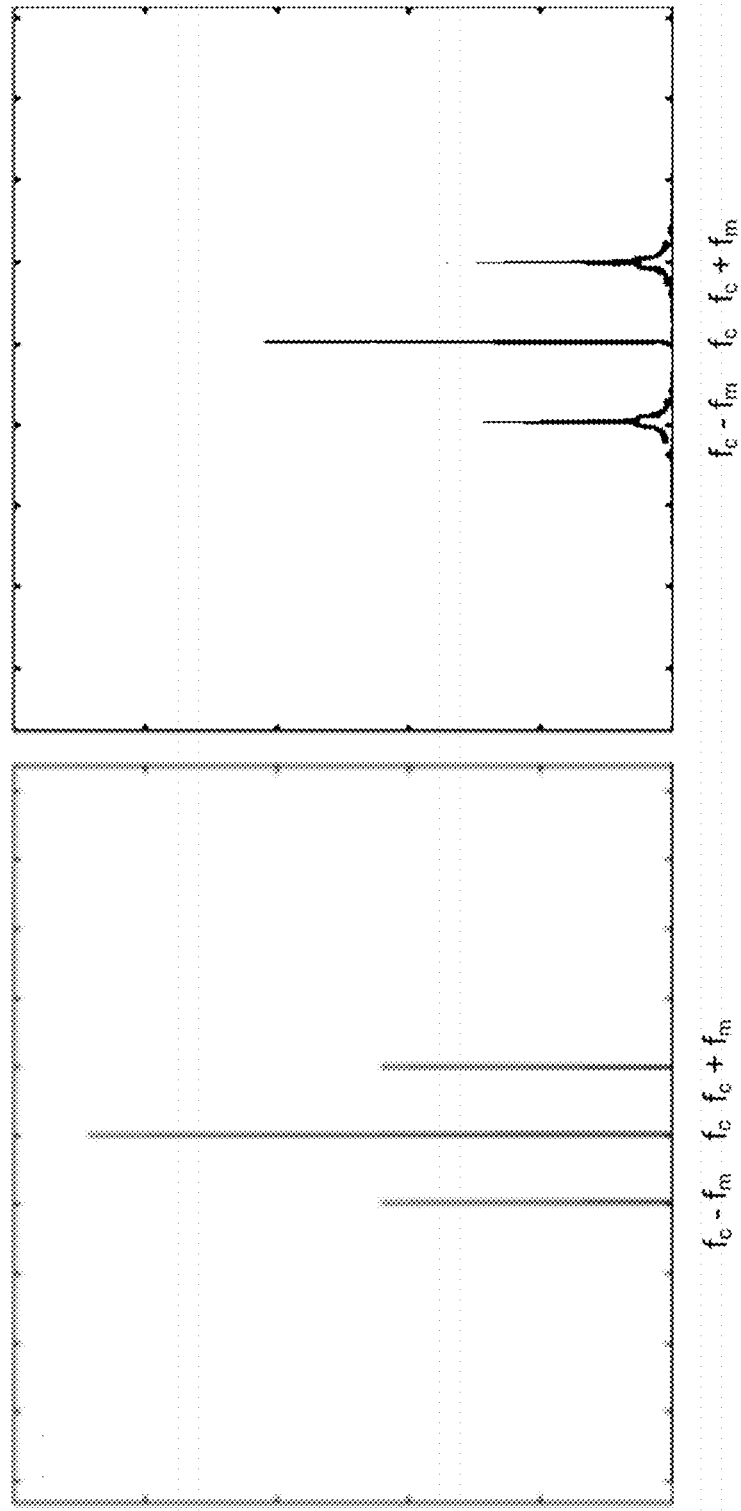
FIG. 2 A-B show spectrum of a sinusoidal amplitude modulated test stimulation signal with and without a jitter component.

In ASSR measurements, neural responses are evoked after application of a sequence of a periodic test stimulation signal. In acoustically evoked ASSR (AASSR), the test stimulation signal may be a sinusoidal amplitude modulated signal (SAM) with a carrier frequency $f_c$ and modulation frequency $f_m$. FIG. 2A shows an example of the corresponding frequency spectrum for such a SAM test stimulation signal in which the carrier frequency $f_c$ determines the specific stimulation location within the cochlea and the modulation frequency $f_m$ (sidebands) determines the temporal fluctuations within the frequency channel in case of unresolved harmonics. FIG. 2B shows the corresponding AASSR frequency spectrum for the case where a jitter component is introduced into the modulation test frequency $f_m$. In electrically evoked ASSR (EASSR), the active electrode contact of the implanted electrode array determines the specific stimulation location within the cochlea and the test stimulation signal may be a periodic pulse train with a repetition rate of the modulation test frequency $f_m$.

When the auditory system receives such a test stimulation signal, the neuronal response signals are locked to the test frequency $f_m$, thereby allowing very frequency-specific objective measurements. (See e.g., Bahmer and Baumann, *Recording and Online Analysis of Auditory Steady State Responses (ASSR) in Matlab*, J. Neurosci. Methods., 2010, 187(1):105-13; Picton et al., *Potentials Evoked by the Sinusoidal Modulation of the Amplitude or Frequency of a Tone*, J. Acoust. Soc. Am., 1987, 82:165-78; Rees et al., *Steady State Evoked Responses to Sinusoidally Amplitude-Modulated Sounds Recorded in Man*, Hear Res. 1986, 23:123-33; Hofmann and Wouters, *Electrically Evoked Auditory Steady State Responses in Cochlear Implant Users*, J. Assoc. Res. Otolaryngol. 2010 June, 11(2):267-82; all of which are incorporated herein by reference in their entireties). Thus embodiments of the present invention provide arrangements to determine the amount of correlation between objective electrophysiologic tests such as ASSR and subjective psychophysical tests.

Figure 3:
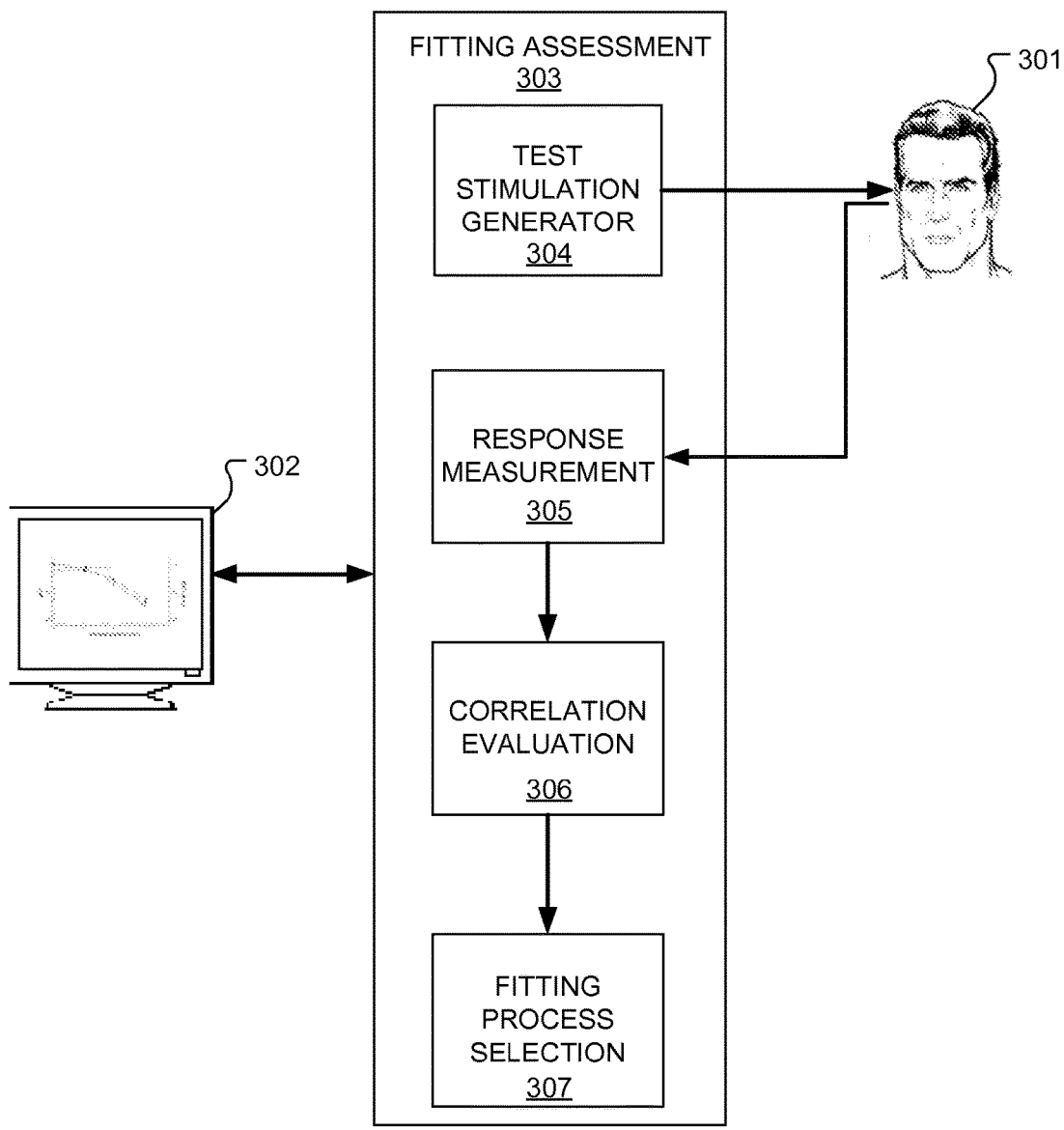
FIG. 3 shows various operational modules in a fitting assessment system according to an embodiment of the present invention.
Figure 4:
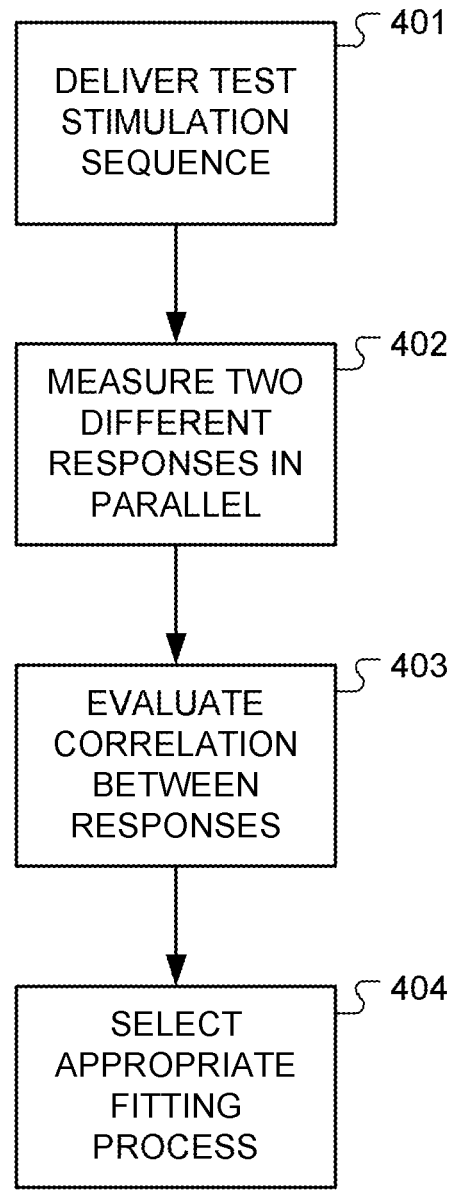
FIG. 4 shows various steps in a fitting assessment process according to an embodiment of the present invention.

FIG. 3 shows various operational modules in a fitting assessment system and FIG. 4 shows various steps in a fitting assessment process according to embodiments of the present invention. The fitting assessment system 303 includes a test stimulation generator 304 that delivers to the cochlear implant patient 301 a test stimulation sequence at a given test frequency, step 401. The test stimulation sequence from the test stimulation generator 304 includes alternating stimulation periods of jittered stimulation in which the test frequency varies due to a jitter variation component, and unjittered stimulation in which the test frequency is constant without a jitter variation component.

Figure 5:
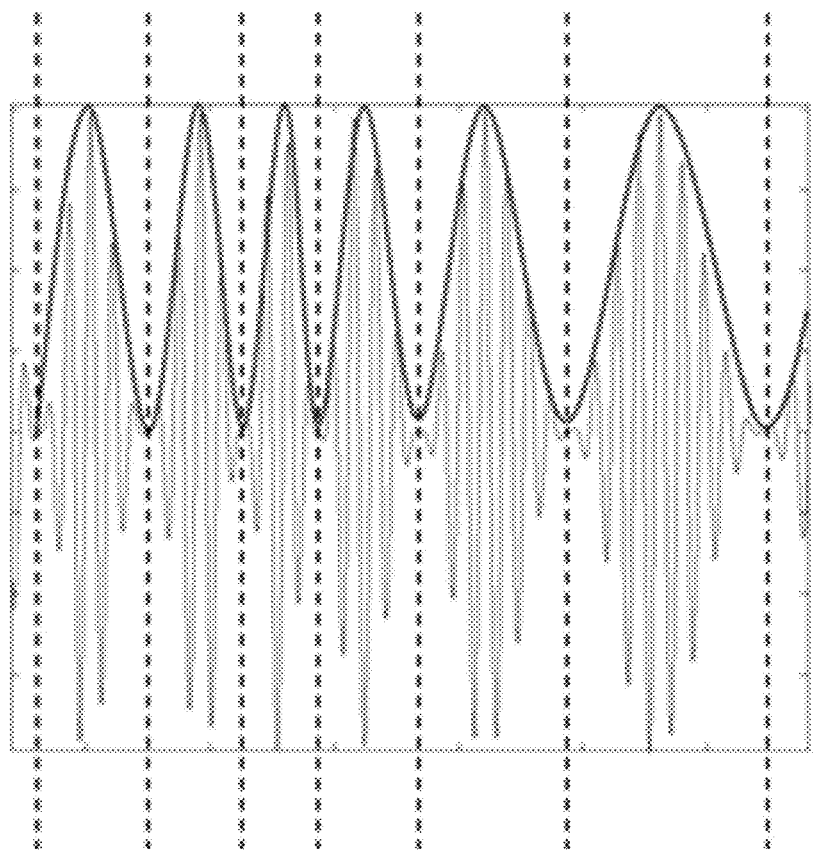
FIG. 5 shows an example waveform for a jittered AASSR stimulus sequence.

For each fitting assessment session, the duration of the test stimulation sequence produced by the test stimulation generator 304 should be long enough to properly establish the physiological steady-state response in the test person; typically about 30 seconds. However, this value is dependent on various different parameters and so may be patient specific; thus any value between 15 and 60 seconds or even more than 60 seconds may be acceptable. The test stimulation generator 304 may specifically deliver an acoustic and/or electric test stimulation sequence to the cochlear implant patient 301. FIG. 5 shows an example waveform for a jittered AASSR stimulus sequence. In various specific embodiments, the jitter variation component produced by the test stimulation generator 304 may create a constant amount of variation in the test frequency during all of the jittered stimulation periods, or it may change the amount of variation in the test frequency between different jittered stimulation periods, and a Gaussian jitter variation component may specifically include standard deviations from 0.2 to 0.8, more specifically from 0.4 to 0.6. A specific test stimulation sequence may be comprised of purely jittered, purely unjittered, or any mix of jittered and unjittered stimulation periods.

The test stimulation generator 304 may deliver stimulation periods with uniform time durations, or stimulation periods with different time durations. It may be advantageous for the test stimulation generator 304 to deliver jittered stimulation periods and unjittered stimulation periods that have the same duration in time so that the auditory system of the cochlear implant patient 301 always has the same time to adapt to a new test stimulation sequence. In case of EASSR that requirement can be fulfilled quite easily, but for AASSR, it may be advantageous to meet another additional requirement in addition. In the jittered stimulation period shown in FIG. 5, the vertically dashed lines separate full sinusoidal wave cycles within the jittered stimulation period. The specific lengths of the individual full wave cycles may vary depending on the specific amount of the jitter variation component. It may be advantageous for AASSR to use only jitter variation patterns that include such full wave cycles so that an entire jittered stimulation period contains multiple full wave cycles.

A response measurement module 305 in the fitting assessment system 303 measures in parallel at least two different responses of the cochlear implant to the test stimulation sequence, step 402. The response measurement module 305 includes an objective measurement submodule that measures an objective electrophysiological response of the cochlear implant patient 301 (e.g., an auditory steady-state response (ASSR) such as an acoustically evoked ASSR (AASSR) and/or an electrically evoked ASSR (EASSR)), and a subjective measurement submodule that measures a subjective psychophysical response of the cochlear implant patient 301 (e.g., based on perception by the cochlear implant patient 301 of the jitter variation component).

A correlation evaluation module 306 evaluates a correlation between the different responses, step 403, to determine an appropriate fitting process for the cochlear implant patient 301, step 404. To that end, the correlation evaluation module 306 may include a fitting process selection submodule that determines an objective electrophysical fitting process as the appropriate fitting process when the correlation is evaluated to be sufficient. When the correlation evaluation module 306 evaluates the correlation to be insufficient, the fitting process selection submodule may further determine a subjective psychophysical fitting process as the appropriate fitting process.

It is important to test the cochlear implant patient with a test stimulation sequence that includes multiple periods of jittered stimulation and unjittered stimulation to allow the patient to subjectively respond and indicate detection of a jittered stimulation period at the same time that an objective electrophysiologic measurement is performed.

Figure 6:
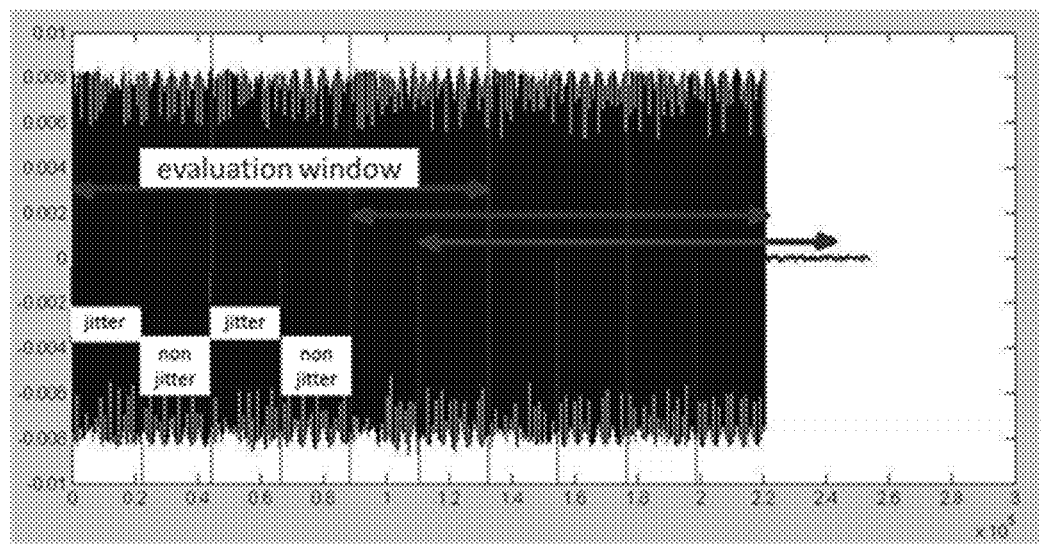
FIG. 6 shows an example of a recorded test signal for a test stimulation sequence containing jittered and unjittered stimulation periods.

For the ASSR signal measurement, an electroencephalogram (EEG) signal can be recorded in response to either an acoustic test stimulation sound source (in the case of AASSR) or an electrical test stimulation sound source (the cochlear implant electrode contacts in the case of EASSR). The analysis window may be shifted in time for the calculation of the ASSR signal. The EEG signal can be measured using implantable or non-implantable recording electrodes, for example, on the scalp and/or the forehead of the patient. FIG. 6 shows an example of an ASSR response recording as a function of recording time (ms) for a test stimulation sequence that contains jittered and unjittered stimulation periods.

Figure 7:
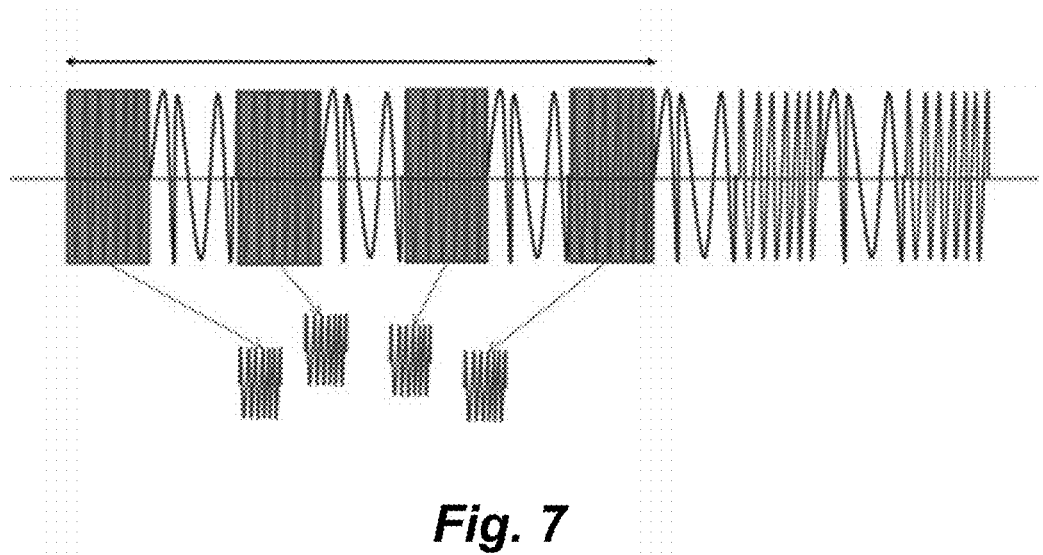
FIG. 7 shows a schematic EEG signal in response to jittered and unjittered stimulation periods.

In order to derive the ASSR signal out of the recorded EEG signal, an evaluation window can defined with a length L, wherein L is at least time T. If lengths L of both the jittered and unjittered stimulation periods are not equal, then the length of the evaluation window should be at least the length of the shortest jittered/unjittered stimulation period within the test stimulation sequence. FIG. 7 shows an EEG signal where the evaluation window extends over 4 jittered/unjittered stimulation periods. The evaluation window may be chosen such that each second period T out of the EEG signal is chosen for further processing (in particular, if a test stimulation sequence includes only identical unjittered stimulation periods). Alternatively, just a single stimulation period may be chosen out of the signal. The filtered data for the chosen stimulation period(s) are then further processed, for example, by averaging the filtered data, calculating a frequency spectrum (e.g. by FFT) of the averaged data, and then deriving the FFT amplitude at $f_c-f_m$ or $f_c+f_m$. Then, the evaluation window can be shifted in time, the evaluation procedure repeated.

Figure 8:
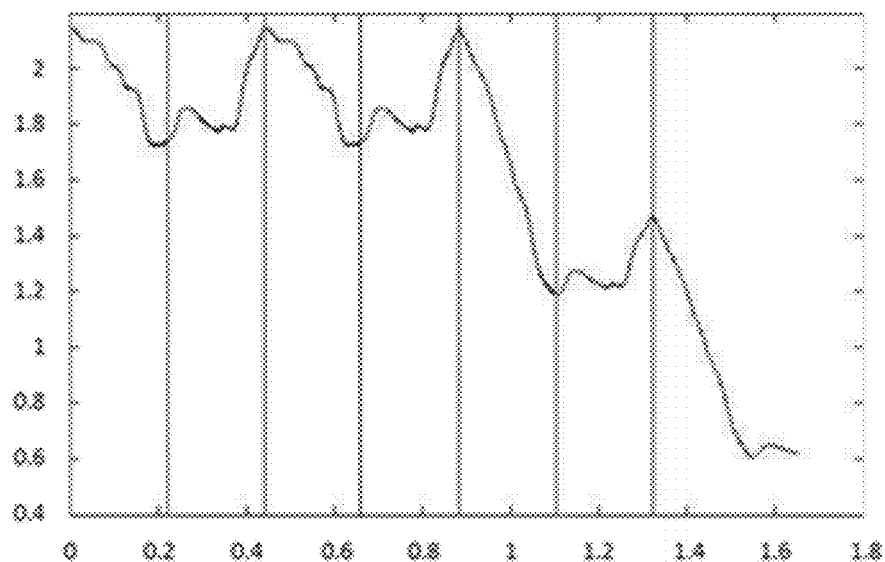
FIG. 8 shows an example waveform of an FFT test analysis.

FIG. 8 shows an example waveform of an FFT test analysis for simulated EASSR values (unnormalized) as a function of time (corresponding to the shifting of the analysis window). The vertical lines indicate the changes between jittered and unjittered stimulation periods. As can be seen in FIG. 8, there will be local maximums and minimums in the measured ASSR signal. Local maximums correspond to when the evaluation window is in a position where it discards all jittered stimulation periods so that only unjittered stimulation periods are taken for averaging and FFT analysis. Similarly, local minimums correspond to when the evaluation window is in a position where it discards all unjittered stimulation periods. The sequence of local maxima and minima in the ASSR signal can be assigned to the specific points of the EEG signal, and further to the test simulation sequence where jittered and unjittered stimulation periods have changed. Thus the beginning of the recording can be identified which previously was unknown because of the unknown delay between the test stimulus sequence and the start of the response signal recording. This knowledge is used for the comparison of this objective electrophysical measurement with the result of the subjective psychophysical test.

In the specific case of EASSR measurements, cancellation of the stimulus artifacts also needs to be considered. Possible methods are suggested by Hoffman and Wouters, *Electrically Evoked Auditory Steady State Responses in Cochlear Implant Users*, J Assoc Res Otolaryngol. 2010 June, 11(2): 267-82 and Hoffman and Wouters, *Improved Electrically Evoked Auditory Steady-State Response Thresholds in Humans*, J Assoc Res Otolaryngol. 2012 August, 13(4):573-89; which are incorporated herein by reference in their entireties.

In the subjective psychophysical test that is performed in parallel to the ASSR recording, a test patient may be asked to differentiate between jittered and unjittered stimulation periods (the perceived signal sounds different). The patient reports when he detects a jittered stimulation period is occurring, or the patient may count the number of jittered stimulation periods. One possible test scenario might be as follows:

Two unjittered tones with different pitches are presented to the test person.

The difference in pitch is increased such that this person can reliably discriminate the two pitches (e.g. discrimination rate is higher than 90%).

A test stimulation sequence as described above then is presented with jittered stimulation periods and the test person has to indicate if he still can discriminate the two tones. Alternatively, the task of the test person may be to report which of the two pitches he/she has perceived as higher.

Then another test stimulation sequence is presented with increased jitter compared to the previous stimulation stream.

Breaks between the test stimulation sequences are optional.

Various other psychophysical tests are feasible, these are just some examples.

Figure 9:
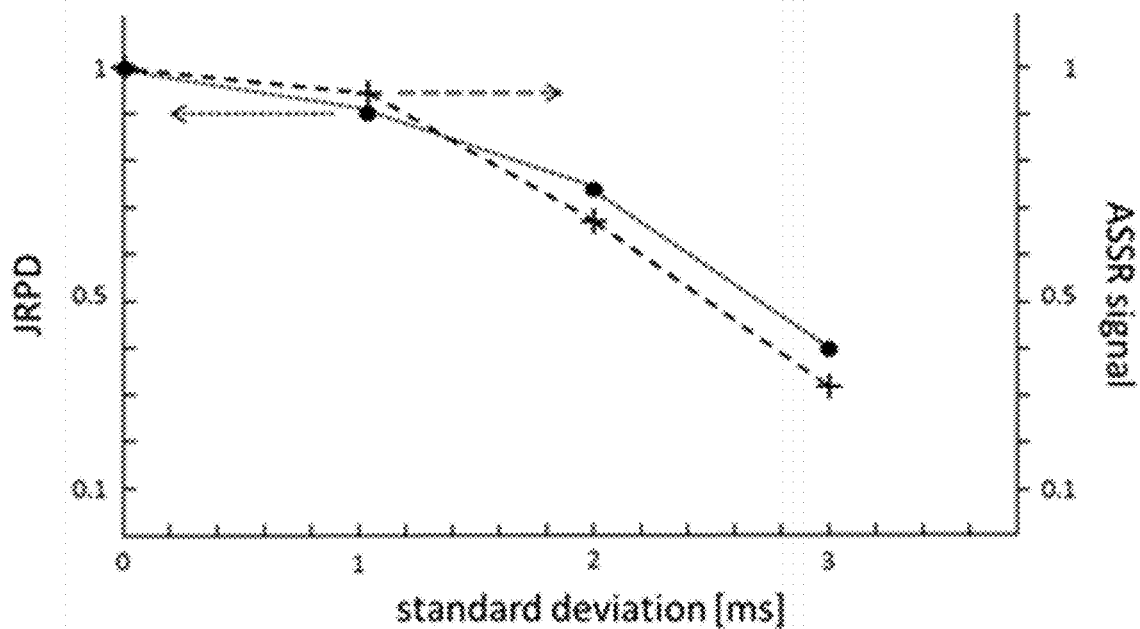
FIG. 9 shows an example schematic of the correlation between ASSR and jittered pitch rate discrimination (JRPD).

In the subjective psychophysical test, the tested patient generally has to provide what is known as a jittered rate pitch discrimination (JRPD). FIG. 9 shows one set of experimental results which indicates that the JRPD decreases with increased standard deviation. Subsequently, the values of the ASSR and the JRPD are normalized (e.g. so that the distance of maximum and minimum ASSR value is 1, and the JRPD for pure unjittered stimulation is 1), and then compared in terms of various correlations, e.g. both values are plotted in one graphic against the standard deviation of the jittered signal (FIG. 9). Possible correlation criteria might include common peaks, same monotony of the recorded signals, sum of means square of distances between corresponding points are below a specific value, etc. If a correlation between both signals can be shown, this correlation may serve as a reference for subsequent electrophysiological measures or fitting procedures, e.g. based on ASSR as an objective measurement. If the pre-test does not show a correlation between both entities a standard psychophysical fitting procedure has to be employed.

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments also can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A fitting assessment system for assessing potential fitting processes for a cochlear implant patient, the system comprising:
    a test stimulation generator that delivers to the cochlear implant patient a test stimulation sequence at a given test frequency, the test stimulation sequence including:
        i. a plurality of jittered stimulation periods in which the test frequency varies due to a jitter variation component, and
        ii. a plurality of unjittered stimulation periods in which the test frequency is constant without a jitter variation component;
    a response measurement module that measures in parallel at least two different responses of the cochlear implant to the test stimulation sequence, the response measurement module including:
        i. an objective measurement submodule that measures an objective electrophysiological response, and
        ii. a subjective measurement submodule that measures a subjective psychophysical response; and
    a correlation evaluation module that evaluates a correlation between the different responses to determine an appropriate fitting process for the cochlear implant patient.

2. The system according to claim 1, wherein the correlation evaluation module includes a fitting process selection submodule that determines an objective electrophysical fitting process as the appropriate fitting process when the correlation is evaluated to be sufficient.

3. The system according to claim 2, wherein the fitting process selection submodule further determines a subjective psychophysical fitting process as the appropriate fitting process when the correlation is evaluated to be insufficient.

4. The system according to claim 2, wherein the subjective measurement submodule measures the subjective psychophysical response based on perception by the cochlear implant patient of the jitter variation component.

5. The system according to claim 2, wherein the objective electrophysical response measured by the objective response submodule includes an auditory steady-state response (ASSR).

6. The system according to claim 5, wherein the ASSR is an acoustically evoked ASSR (AASSR).

7. The system according to claim 5, wherein the ASSR is an electrically evoked ASSR (EASSR).

8. The system according to claim 2, wherein the test stimulation generator delivers an acoustic test stimulation sequence to the cochlear implant patient.

9. The system according to claim 2, wherein the test stimulation generator delivers an electrical test stimulation sequence to the cochlear implant patient.

10. The system according to claim 2, wherein the test stimulation generator generates a constant amount of variation in the test frequency in all of the jittered stimulation periods.

11. The system according to claim 2, wherein the test stimulation generator changes the amount of variation in the test frequency between different jittered stimulation periods.

12. The system according to claim 2, wherein the test stimulation generator delivers stimulation periods with uniform time durations.

13. The system according to claim 2, wherein the test stimulation generator delivers stimulation periods with different time durations.

14. The system according to claim 2 wherein the test stimulation generator delivers the jittered stimulation periods and the unjittered stimulation periods with equal time durations.

15. A method for assessing potential fitting processes for a cochlear implant patient, the method comprising:
    delivering to the cochlear implant patient a test stimulation sequence at a given test frequency, the test stimulation sequence including:
        i. a plurality of jittered stimulation periods in which the test frequency varies due to a jitter variation component, and ii. a plurality of unjittered stimulation periods in which the test frequency is constant without a jitter variation component;

measuring in parallel at least two different responses of the cochlear implant to the test stimulation sequence, the different responses including:

i. an objective electrophysiological response, and ii. a subjective psychophysical response; and evaluating a correlation between the different responses to determine an appropriate fitting process for the cochlear implant patient.

16. The method according to claim 15, further comprising:

determining an objective electrophysical fitting process as the appropriate fitting process when the correlation is evaluated to be sufficient.

17. The method according to claim 15, further comprising:

determining a subjective psychophysical fitting process as the appropriate fitting process when the correlation is evaluated to be insufficient.

18. The method according to claim 15, wherein the subjective psychophysical response is based on perception by the cochlear implant patient of the jitter variation component.

19. The method according to claim 15, wherein the objective electrophysical response includes an auditory steady-state response (ASSR).

20. The method according to claim 19, wherein the ASSR is an acoustically evoked ASSR (AASSR).

21. The method according to claim 19, wherein the ASSR is an electrically evoked ASSR (EASSR).

22. The method according to claim 15, wherein the test stimulation sequence is acoustically delivered to the cochlear implant patient.

23. The method according to claim 15, wherein the test stimulation sequence is electrically delivered to the cochlear implant patient.

24. The method according to claim 15, wherein the amount of variation in the test frequency due to the jitter variation component is constant in all of the jittered stimulation periods.

25. The method according to claim 15, wherein the amount of variation in the test frequency due to the jitter variation component changes between different jittered stimulation periods.

26. The method according to claim 15, wherein the stimulation periods have uniform time durations.

27. The method according to claim 15, wherein the stimulation periods have different time durations.

28. The method according to claim 15, wherein the jittered stimulation periods and the unjittered stimulation periods have equal time durations.

* * * * *